United States Patent [19]

Kamaya et al.

[11] Patent Number: 4,822,898

[45] Date of Patent: Apr. 18, 1989

[54] ASCORBIC ACID OR ERYTHORBIC ACID DERIVATIVES

[75] Inventors: Kazuo Kamaya, Toyonaka; Yukihisa Takisawa, Misawa, both of Japan

[73] Assignee: Sumitomo Chemical Company, Limited, Osaka, Japan

[21] Appl. No.: 906,373

[22] Filed: Sep. 12, 1986

[30] Foreign Application Priority Data

Sep. 20, 1985 [JP] Japan .................. 60-209499
Sep. 24, 1985 [JP] Japan .................. 60-211937

[51] Int. Cl.$^4$ .................................. C007 307/62
[52] U.S. Cl. .................................. 549/317
[58] Field of Search .................. 549/317

[56] References Cited

U.S. PATENT DOCUMENTS

| | | | |
|---|---|---|---|
| 2,350,435 | 6/1944 | Wells et al. | 549/317 |
| 2,408,897 | 10/1946 | Walls et al. | 549/317 |
| 2,728,661 | 12/1955 | Thirtle et al. | |
| 4,324,778 | 4/1982 | Davis | 514/450 |
| 4,329,290 | 5/1982 | Sawyer et al. | 549/316 |

OTHER PUBLICATIONS

English translation of Ja 49-87655.
T. Imai et al, Chemical Abstracts, 82:123533b (1975).
M. Creighton et al, Jour.Org.Chem., vol.13 (1948), pp. 613–615.
Chemical Abstracts, vol. 43, no. 2, Jan. 25, 1949 (col. 576c–d).
Chemical Abstracts, vol. 82, no. 13, Mar. 31, 1975 (p 540, col 2, Abstract No. 86562n).

*Primary Examiner*—Glennon H. Hollrah
*Assistant Examiner*—Mark W. Russell
*Attorney, Agent, or Firm*—Stevens, Davis, Miller & Mosher

[57] ABSTRACT

An ascorbic acid or erythorbic acid derivative represented by the following general formula:

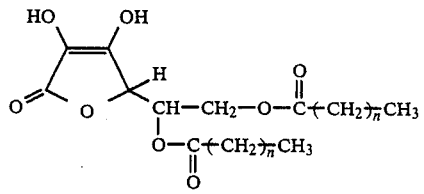

wherein n represents an integer of 4 to 20; and a process for producing said ascorbic acid or erythorbic acid derivative which comprises heat-treating 2,5,6-triacyl-substituted-ascorbic acid or -erythorbic acid represented by the following general formula:

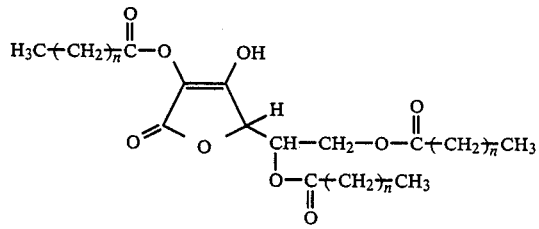

wherein n represents an integer of 4 to 20, in the presence of water and/or a lower aliphatic alcohol at a temperature of 30° C. to 100° C. and thereby selectively eliminating only the acyl group of the 2-position.

1 Claim, No Drawings

ASCORBIC ACID OR ERYTHORBIC ACID DERIVATIVES

BACKGROUND OF THE INVENTION

1. Field of the Invention

The present invention relates to ascorbic acid or erythorbic acid derivatives represented by the following general formula (I)a:

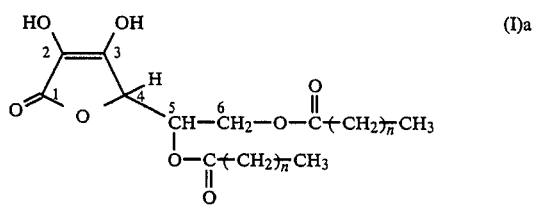

wherein n represents an integer of 12 to 20, which are novel compounds not found in literature, as well as to a process for producing ascorbic acid or erythorbic acid derivatives represented by the following general formula (I)b:

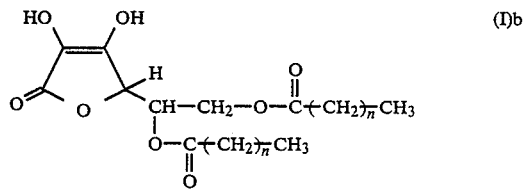

wherein n represents an integer of 4 to 20.

2. Prior Art

Having excellent fat-solubility and antioxidative property, the ascorbic acid (erythorbic acid) derivatives represented by the above-mentioned general formula (I)a and (I)b are useful in themselves alone or in combination with tocopherol or the like as an antioxidant for foodstuffs and living bodies.

Although ascorbic acid (erythorbic acid) is known as an antioxidant for foodstuffs and the like, it is not satisfactory in fat-solubility and antioxidative property. Thus, a variety of acyl-substituted derivatives of ascorbic acid have so far been synthesized tentatively. For example, Japanese Patent Kokai (Laid-Open) No. 87,655/74 disclosed a process for producing 5,6-diacyl substituted derivatives represented by the general formula (I)a or (I)b wherein n was 8 or less. However, these 5,6-diacyl substituted derivatives were yet insufficient in fat-solubility and antioxidative property.

Apart from them, acyl substituted derivatives of ascorbic (erythorbic) acid having acyl substituents on 2,6-positions, 2,5,6-positions or 2,3,5,6-positions are also known. Although an increase in the number of acyl substituent is accompanied by an increase in fat-solubility, an antioxidative property can be exhibited only when 2-position and/or 3-position are(is) not acyl-substituted. Accordingly, these polyacyl-substituted derivatives cannot be used as an antioxidant.

As the process for producing acyl-substituted derivatives of ascorbic acid or erythorbic acid, a variety of processes are known. According to the usual acylating process, monoacylation, diacylation, triacylation, tetraacylation and so on take place successively, and these acylations usually take place first at the 6-position and then at 2, 5 and 3-positions, in the mentioned order. This means that the only diacyl substituted derivative obtainable is 2,6-diacyl substituted derivative.

In Japanese Patent Kokai (Laid-Open) No. 87,655/74, there was disclosed a process for selectively producing only 5,6-diacyl substituted derivative which comprises reacting ascorbic acid with an anhydride or a halide of lower fatty acid. However, when applied to fatty acids having 4 or more carbon atoms, this process could not yield the ascorbic acid or erythorbic acid derivatives represented by the general formula (I)b.

SUMMARY OF THE INVENTION

In view of above, the present inventors conducted many studies with the aim of developing ascorbic acid (erythorbic acid) derivatives excellent in fat-solubility and antioxidative property. As the result, they succeeded in developing the ascorbic acid (erythorbic acid) derivatives represented by the general formula (I)a which are novel compounds.

Further, the inventors studied an advantageous production process of 5,6-diacyl substituted derivatives of ascorbic acid or erythorbic acid represented by the general formula (I)b. As the result, it was found that the aimed compounds can easily be obtained by selectively eliminating only the 2-acyl group from the industrially easily producible 2,5,6-triacyl substituted derivative of ascorbic acid or erythorbic acid. Based on this finding, the present invention was accomplished.

DETAILED DESCRIPTION

In the ascorbic acid (erythorbic acid) derivatives represented by the general formula (I)a, the number represented by "n" has an important meaning from the viewpoint of functional effect. Thus, when n is in the range from 12 to 20, the derivatives exhibit quite excellent effects in both fat-solubility and antioxidative property. Particularly regarding the antioxidative activity in living bodies, derivatives wherein n is smaller than 12 can exhibit no effect at all or can exhibit only a quite poor effect, while derivatives wherein n is in the range from 12 to 20 exhibit a quite excellent antioxidative activity.

Such ascorbic acid (erythorbic acid) derivatives represented by the general formula (I)a or (I)b can be produced by, for example, acylating ascorbic acid (erythorbic acid) to obtain its 2,5,6-triacyl substituted derivative, followed by selectively deacylating only the 2-acyl group.

In this production process, the first step or the acylation is carried out according to the conventional method of acylation. Thus, it is carried out by reacting ascorbic acid (erythorbic acid) with an acylating agent such as straight chain saturated aliphatic monocarboxylic acid having 14 to 22 carbon atoms or its acid halide (e.g. acid chloride) or its acid anhydride in the presence of an acid catalyst or a basic condensing agent.

The second step of the selective deacylation of 2-acyl group is carried out by heat-treating the 2,5,6-triacyl substituted derivative of ascorbic acid (erythorbic acid) obtained in the first step represented by the following general formula (II):

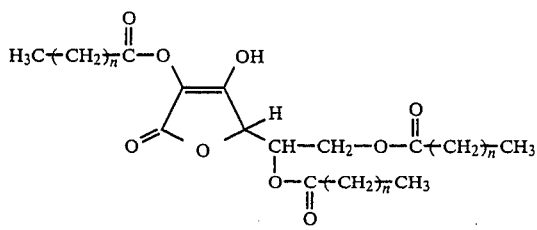
(II)

wherein n represents an integer of 4 to 20, provided that n represents an integer of 12 to 20 when the derivative of the general formula (I)a is to be produced, in water and/or lower aliphatic alcohol at a temperature of 30° C. to 100° C. Usually, the heat-treatment of the second step readily progresses in the presence of a nucleophilic reagent such as methanol and the like and, if necessary, a weakly acidic compound such as acetic acid.

In the 2,5,6-triacyl substituted derivative of ascorbic acid or erythorbic acid represented by the general formula (II) which is used as a starting compound in the invention, examples of the acyl group include octanoyl group, myristoyl group, palmitoyl group, stearoyl group, eicosanoyl group, docosanoyl group and the like. Such 2,5,6-triacyl substituted derivatives of ascorbic acid or erythorbic acid can easily be produced by reacting ascorbic acid or erythorbic acid with an acid chloride or an acid anhydride having any of the above-mentioned acyl groups in the presence of a base such as pyridine, picoline, triethylamine and the like.

The 2,5,6-triacyl substituted derivative of ascorbic acid or erythorbic acid formed in the above-mentioned manner may be put to use as a starting material of the deacylation of the invention either after isolation from the reaction mixture or without isolation from reaction mixture, i.e. directly in the form of the reaction mixture itself.

The deacylation is carried out by heat-treating a 2,5,6-triacyl substituted derivative of ascorbic acid or erythorbic acid in the presence of a specified substance (referred to as "reactant", hereinafter) and, if necessary, in the presence of a catalyst at a temperature of 30° C. to 100° C., preferably 40° C. to 90° C.

As said reactant, a lower aliphatic alcohol such as methanol, ethanol, n-propyl alcohol, isopropyl alcohol, n-butyl alcohol and the like or water is used. If desired, a mixture consisting of two or more members selected from the above-mentioned reactants may be used for this purpose.

Usually, the reactant is used in an amount of 1 to 20 parts by weight per 1 part by weight of the 2,5,6-triacyl substituted derivative of ascorbic acid or erythorbic acid.

Examples of said catalyst include lower fatty acids such as acetic acid, propionic acid and the like; mineral acids such as hydrochloric acid, sulfuric acid and the like; and alkalis such as sodium hydroxide, potassium hydroxide and the like. The catalyst is used in an amount of 0 to 5 parts by weight per 1 part by weight of the 2,5,6-triacyl substituted derivative of ascorbic acid or erythorbic acid.

By the above-mentioned deacylation, only the acyl group of 2-position is selectively eliminated from the starting 2,5,6-triacyl substituted derivative of ascorbic acid or erythorbic acid, and the intended 5,6-diacyl substituted derivative of ascorbic acid or erythorbic acid represented by the general formula (I)a or (I)b is easily obtained in a high yield.

Concrete examples of the ascorbic acid (erythorbic acid) derivative represented by the general formula (I)a or (I)b thus obtained, include 5,6-di-O-myristoyl-ascorbic acid (or -erythorbic acid), 5,6-di-O-palmitoyl-ascorbic acid (or -erythorbic acid), 5,6-di-O-stearyl-ascorbic acid (or -erythorbic acid), 5,6-di-O-eicosanoyl-ascorbic acid (or -erythorbic acid), 5,6-di-O-docosanoyl-ascorbic acid (or -erythorbic acid), and the like.

Referring to the following non-limitative examples, the invention will further be illustrated.

EXAMPLE 1

At 20° C., 74.05 g (0.3 mole) of myristoyl chloride was dropwise added to a mixture consisting of 17.61 g (0.1 mole) of ascorbic acid and 150 g of pyridine over a period of 2 hours, and the resulting mixture was stirred at that temperature for 5 hours.

After completion of the reaction, chloroform and 10% hydrochloric acid were added to the reaction mixture to perform an extraction. The chloroform layer was washed successively with 10% hydrochloric acid and water and then the chloroform was distilled off. The crystalline product thus obtained was recrystallized first from n-hexane and subsequently from ether. Thus, 41 g of 2,5,6-trimyristoyl-ascorbic acid, melting at 86°–89° C., was obtained.

Then, 30.0 g (0.0372 mole) of the 2,5,6-trimyristoyl-ascorbic acid was mixed with 34 g of glacial acetic acid and 150 g of methanol, and the mixture was stirred at 65° C. for 8 hours. After completion of the reaction, 300 g of water and 200 g of toluene were added to the reaction mixture and an extraction was performed. By distilling off toluene from the toluene layer, there was obtained a crude crystalline product. After adding a solvent mixture consisting of 30 g of chloroform and 70 g of n-hexane to the crude crystalline product, it was heated to obtain a homogeneous solution.

The solution was allowed to stand at room temperature and the resulting crystal was collected by filtration. By again recrystallizing it from a mixture consisting of chloroform and n-hexane, 17.0 g of 5,6-di-O-myristoyl-L-ascorbic acid was obtained.

m.p.: 80°–81° C.

$[\alpha]_D^{20}$: −26.7° C. (CHCl₃).

¹H-NMR spectrum (270 MHz).

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 40 | 4 | 4 | 2 | 1 | 1 |
| Multiplicity | t | b | m | t | m | d | m | d: Doublet, t: Triplet, m: Multiplet, b: Broad

EXAMPLE 2

According to the procedure of Example 1, ascorbic acid and palmitoyl chloride were reacted to obtain 2,5,6-tripalmitoyl-ascorbic acid. Its 31.0 g (0.0348 mole) was mixed with 150 g of methanol and 34.7 g of glacial acetic acid, and the mixture was heated at 65° C. for 7 hours with stirring.

After completion of the reaction, 200 g of toluene and 300 g of water were added to the reaction mixture to perform an extraction. By distilling off toluene from the toluene layer, there was obtained a crude crystalline product. It was recrystallized from a solvent mixture consisting of 20 g of chloroform and 80 g of n-hexane to obtain 19.8 g of a crystalline product.

By repeatedly recrystallizing it from a mixture of chloroform and n-hexane, 8.5 g of 5,6-di-O-palmitoyl-L-ascorbic acid was obtained.

m.p.: 85°–86° C.
$[\alpha]_D^{20}$: −26.2° (CHCl$_3$).
$^1$H-NMR spectrum (270 MHz).

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 48 | 4 | 4 | 2 | 1 | 1 |
| Multiplicity | t | b | m | t | m | d | m |

EXAMPLE 3

According to the procedure of Example 1, erythorbic acid and palmitoyl chloride were reacted to obtain 2,5,6-tripalmitoyl-erythorbic acid. Its 31.0 g (0.0348 mole) was mixed with 150 g of methanol and 34.7 g of glacial acetic acid, and the mixture was heated at 65° C. for 7 hours with stirring.

Thereafter, the treatment of Example 2 was repeated to obtain 9.1 g of crystalline 5,6-di-O-palmitoyl-D-erythorbic acid.

m.p.: 71°–73° C.
$[\alpha]_D^{20}$: +11.0° (CHCl$_3$).
$^1$H-NMR spectrum (270 MHz).

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 48 | 4 | 4 | 2 | 1 | 1 |
| Multiplicity | t | b | m | m | m | d | m |

EXAMPLE 4

According to the procedure of Example 1, ascorbic acid was reacted with stearyl chloride to obtain 2,5,6-tristearyl-ascorbic acid. Its 23.0 g (0.0236 mole) was mixed with 115 g of methanol and 23.0 g of glacial acetic acid, and the mixture was heated at 65° C. for 13 hours with stirring.

Thereafter, the procedure of Example 2 was repeated to obtain 6.1 g of crystalline 5,6-di-O-stearyl-L-ascorbic acid.

m.p.: 83°–85° C.
$[\alpha]_D^{20}$: −24.0° (CHCl$_3$).
$^1$H-NMR spectrum (270 MHz).

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 56 | 4 | 4 | 2 | 1 | 1 |
| Multiplicity | t | b | m | t | m | d | m |

EXAMPLE 5

According to the procedure of Example 1, ascorbic acid and docosanoyl chloride were reacted to obtain 2,5,6-tri-docosanoyl-ascorbic acid. Its 15.0 g (0.0131 mole) was mixed with 75 g of methanol and 15 g of glacial acetic acid, and the mixture was heated for 10 hours with stirring.

Thereafter, the procedure of Example 2 was repeated to obtain 4.8 g of crystalline 5,6-di-O-docosanoyl-L-ascorbic acid.

m.p.: 85°–87° C.
$[\alpha]_D^{20}$: −20.0° (CHCl$_3$).
$^1$H-NMR spectrum (270 MHz).

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 72 | 4 | 4 | 2 | 1 | 1 |
| Multiplicity | t | b | m | t | m | d | m |

REFERENTIAL EXAMPLE 1

Solubility of 5,6-di-O-stearyl-ascorbic acid in benzene was measured by the usual method. As the result, it was found to be 1.6 mg/1 ml benzene at 23° C.

Solubility of 6-mono-O-stearyl-ascorbic acid in benzene was measured in the same manner as above. As the result, it was found to be 0.15 mg/1 ml benzene at 23° C.

REFERENTIAL EXAMPLE 2

In order to compare the in vivo antioxidative activity of the compound of the invention with that of comparative compound, an experimental oxidation was carried out, using a liposome system (artificial membrane) as a model of readily oxidizable biological membrane.

As the liposome system, soybean phosphatidylcholine having unsaturated fatty ester group which is readily oxidizable and resembles living body was selected and used as a soybean liposome system. Further, dimyristoyl phosphatidylcholine not oxidizable, was used as dimyristoyl liposome system.

The procedure of experiment was as mentioned below. The results are shown in Table 1.

Experimental Procedure

In a 0.1M aqueous solution of sodium chloride, a liposome of soybean phosphatidyl-choline (soybean PC) was prepared. As a water-soluble chain initiating agent, 2,2′-azobis(2-amidinopropane) hydrochloride (AAPH) was added to the aqueous system so that the concentration of the chain initiating agent reached 30 mM. Then, an oxidation was carried out at 37° C. in the presence of air.

The radical formed by the thermal decomposition of AAPH attacks the lipide present in the soybean PC liposome to start a spontaneous oxidation. If an ascorbic acid derivative is added to this system, it captures the radical yielded from AAPH and the peroxy radical yielded from lipide to suppress the oxidation. When the ascorbic acid derivative has been completely consumed, the oxidation progresses rapidly.

The period during which the oxidation is suppressed is called induction period (t inh). A longer (t inh) means a higher antioxidative property.

Liposome of dimyristoyl phosphatidyl-choline (dimyristoyl PC) is also prepared in the same manner as above.

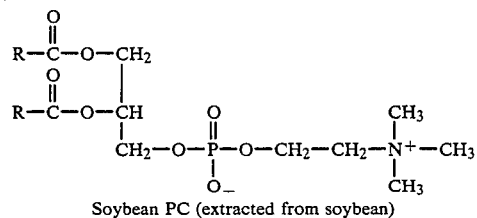

Soybean PC (extracted from soybean)

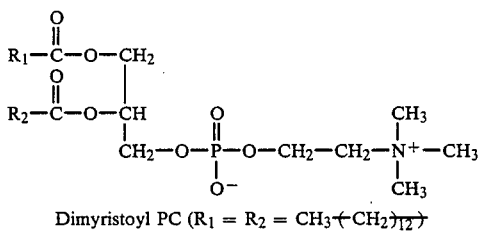

Dimyristoyl PC ($R_1 = R_2 = CH_3(CH_2)_{12}$)

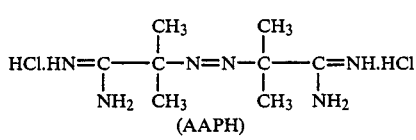

(AAPH)

ascorbic acid is perfectly retained in liposome system. Thus, it has been found that, in a modellized biological system, 5,6-di-palmitoyl-ascorbic acid superior in retainability is superior as an antioxidant.

EXAMPLE 6

A mixture consisting of 5 g (0.009 mole) of 2,5,6-trioctanoyl-ascorbic acid, 25 g of methanol and 5 g of glacial acetic acid was heated at 45° C. for 15 hours with stirring.

After completion of the reaction, 100 ml of ether and 40 ml of water were added to the reaction mixture and an extraction was performed. After drying the ether layer over anhydrous magnesium sulfate, the ether was distilled off and the residue was distilled under reduced pressure to remove the methyl n-octanoate formed as a by-product.

The undistilled matter which had crystallized at room temperature was recrystallized from n-hexane to obtain 3.28 g of 5,6-di-O-octanoyl-ascorbic acid as a white-colored crystalline product.

Yield: 85.0%.

m.p.: 64°–66° C.

$^1$H-NMR spectrum (270 MHz).

TABLE 1

| Run No. | Soybean PC (mM) | Antioxidant | Concentration of the antioxidant (μM) | Dimyristoyl PC (mM) | Antioxidant | Concentration of the antioxidant (μM) | AAPH (mM) | t inh (sec) |
|---|---|---|---|---|---|---|---|---|
| 1 | 12.7 | 5,6-Di-octanoyl-ascorbic acid | 150 | 14.7 | — | — | 30 | 3,390 |
| 2 | 12.7 | — | — | 14.7 | 5,6-Di-octanoyl-ascorbic acid | 150 | 30 | 3,510 |
| 3 | 12.7 | 5,6-Di-palmitoyl-ascorbic acid | 100 | 14.7 | — | — | 30 | 2,070 |
| 4 | 12.7 | — | — | 14.7 | 5,6-Di-palmitoyl-ascorbic acid | 100 | 30 | 0 |

In the system of Table 1, dimyristoyl PC liposome and readily oxidizable soybean PC liposome are both present in the system and an antioxidant for either one of them is added thereto.

The results shown in the table demonstrate that, in Run No. 2, "t inh" of soybean PC reaches 3,510 and an antioxidative activity is exhibited although 5,6-di-O-octanoyl-ascorbic acid has been added into the dimyristoyl PC. This suggests that the 5,6-di-O-octanoyl-ascorbic acid has been transferred from dimyristoyl PC into soybean PC and has captured radicals in the soybean PC. This means that 5,6-di-O-octanoyl-ascorbic acid moves forward and backward between the two liposomes and it is difficult to fix in its nature in one liposome, so that it is difficult to leave in a living body when administered to living organisms.

On the other hand, as Run No. 4 demonstrates it, 5,6-di-O-palmitoyl-ascorbic acid added to dimyristoyl PC is tightly held in the dimyristoyl PC, so that the soybean PC is rapidly oxidized by the radicals generated from AAPH, as the result of which "t inh" is equal to zero.

As above, 5,6-dioctanoyl-ascorbic acid is poor in retainability in liposome system, while 5,6-di-palmitoyl-

| Chemical shift (ppm) | 0.88 | 1.28 | 1.60 | 2.34 | 4.40 | 4.96 | 5.45 |
|---|---|---|---|---|---|---|---|
| Integral ratio (H) | 6 | 16 | 4 | 4 | 2 | 1 | 1 |
| Multiplicity | t | b | m | t | m | d | m | d: Doublet, t: Triplet, m: Multiplet, b: Broad

Molecular weight: 428 (FD-MS spectroscopy).

EXAMPLE 7

Mixtures consisting of 2 g of 2,5,6-trimyristoyl-ascorbic acid, 10 g of a solvent (varied) mentioned in Table 2 and 2 g of catalyst (varied) were deacylated under the reaction conditions mentioned in Table 2.

The yield of 5,6-di-O-myristoyl-ascorbic acid in each run, calculated from its content in the reaction mixture, was as shown in Table 2.

The content of 5,6-di-O-myristoyl-ascorbic acid in the reaction mixture was calculated from UV absorption at 245 nm, taking the 5,6-di-O-myristoyl-ascorbic acid prepared in Example 9 (mentioned later) showing an area percentage of 97.8% in liquid chromatogram as a standard substance.

TABLE 2

| No. | Solvent | Catalyst | Reaction temperature(°C.) | Reaction time (hrs) | Yield (%) |
|-----|---------|----------|---------------------------|---------------------|-----------|
| 1 | Water | Acetic acid | 90 | 3.5 | 78.4 |
| 2 | Methanol | Acetic acid | 65 | 8.5 | 95.0 |
| 3 | Ethanol | Acetic acid | 70 | 11 | 94.1 |
| 4 | Isopropyl alcohol | Acetic acid | 90 | 13 | 78.2 |
| 5 | Methanol | 1% HCl | 65 | 5 | 85.0 |
| 6 | Methanol | 1% $H_2SO_4$ | 65 | 5.5 | 85.1 |
| 7 | Methanol | 0.5% NaOH | 65 | 5.5 | 90.3 |
| 8 | Methanol | — | 65 | 10 | 91.1 |

EXAMPLE 8

A mixture consisting of 31.0 g (0.0348 mole) of 2,5,6-tripalmitoyl-erythorbic acid, 150 g of methanol and 34.7 g of glacial acetic acid was heated at 65° C. for 7 hours.

After completion of the reaction, the yield of 5,6-di-O-palmitoyl-erythrobic acid, calculated from its content in the reaction mixture, was 94.0%.

Then, toluene and water were added to the reaction mixture, and an extraction was performed.

After distilling off toluene from the toluene layer, the resulting crystalline product was recrystallized from 1:4 (by weight) mixture of chloroform and n-hexane to obtain 19.3 g of 5,6-di-O-palmitoyl-erythrobic acid.

Yield: 85.0%.
m.p.: 71°–73° C.
$[\alpha]_D^{20}$: +11.0° ($CHCl_3$).

EXAMPLE 9

A mixture consisting of 20.0 g (0.0248 mole) of 2,5,6-tri-myristoyl-ascorbic acid, 100 g of ethanol and 20 g of 1% hydrochloric acid was heated at 70° C. for 6 hours with stirring.

After completion of the reaction, the yield of 5,6-di-myristoyl-ascorbic acid, calculated from its content in the reaction mixture, was 84.0%.

Toluene and water were added to the reaction mixture, and an extraction was performed. After distilling off toluene from the toluene layer, the resulting crystalline product was recrystallized from 1:6 (by weight) mixture of chloroform and n-hexane to obtain 14.8 g of 5,6-di-O-myristoyl-ascorbic acid.

Yield: 80.0%.
m.p.: 80°–81° C.
$^1$H-NMR spectrum (270 MHz).

| Chemical shift (ppm) | 0.88 | 1.28 | 1.60 | 2.34 | 4.4 | 4.96 | 5.45 |
|---|---|---|---|---|---|---|---|
| Integral ratio (H) | 6 | 40 | 4 | 4 | 2 | 1 | 1 |
| Multiplicity | t | b | m | t | m | d | m |

Molecular weight: 597 (SIMS spectroscopy).
$[\alpha]_D^{20}$: −26.7° ($CHCl_3$).

REFERENTIAL EXAMPLE 3

A mixture consisting of 12.8 g (0.0727 mole) of ascorbic acid, 49.3 g (0.182 mole) of n-octanoic acid anhydride and 0.2 g of potassium hydrogen sulfate was heated at 110°–130° C. for 2.5 hours with stirring. After completion of the reaction, the reaction mixture was cooled and extracted with a mixture consisting of 50 g of water, 50 g of toluene and 50 g of ethyl acetate. After separating the mixture into layers, the organic layer was washed with water and the solvent was distilled off therefrom. The residue was left standing at 5° C. for 12 hours, and then the resulting crystalline product was recrystallized from hot n-hexane to obtain 1.7 g of a crystal melting at 72°–75° C.

As analyzed by $^1$H-NMR spectroscopy at 270 MHz, it was identified as 2,5,6-tri-O-octanoyl-ascorbic acid. No 5,6-di-O-octanoyl-ascorbic acid was obtained in this experiment.

As analyzed by SIMS spectroscopy, the compound obtained above had a molecular weight of 554.

$^1$H-NMR spectrum (270 MHz).

| Chemical shift (ppm) | 0.88 | 1.28 | 1.6 | 2.3 | 2.5 | 4.35 | 5.2 | 5.55 |
|---|---|---|---|---|---|---|---|---|
| Integral ratio (H) | 9 | 24 | 6 | 4 | 2 | 2 | 1 | 1 |
| Multiplicity | t | b | m | t | t | m | s | m | s: Singlet

What is claimed is:

1. An ascorbic acid or erythorbic acid derivative represented by the following general formula (I)a:

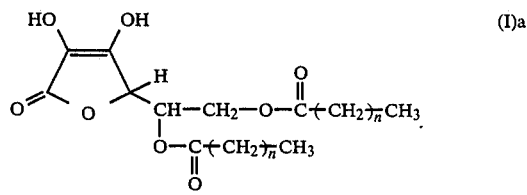

(I)a wherein n represents an integer of 12 to 20.

* * * * *